(12) United States Patent
Gebauer et al.

(10) Patent No.: US 10,094,481 B2
(45) Date of Patent: Oct. 9, 2018

(54) DEVICE FOR DELIVERY OF SAMPLE FLUID

(71) Applicant: GE HEALTHCARE BIO-SCIENCES AB, Uppsala (SE)

(72) Inventors: Klaus Gebauer, Uppsala (SE); Ekta Mahajan, San Francisco, CA (US); Eric Faldt, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 418 days.

(21) Appl. No.: 14/385,516

(22) PCT Filed: Mar. 28, 2013

(86) PCT No.: PCT/SE2013/050357
§ 371 (c)(1),
(2) Date: Sep. 16, 2014

(87) PCT Pub. No.: WO2013/147697
PCT Pub. Date: Oct. 3, 2013

(65) Prior Publication Data
US 2015/0041009 A1 Feb. 12, 2015

(30) Foreign Application Priority Data
Mar. 30, 2012 (SE) ...................... 1250318

(51) Int. Cl.
*F16K 11/10* (2006.01)
*F16K 15/14* (2006.01)
(Continued)

(52) U.S. Cl.
CPC ........... *F16K 11/10* (2013.01); *A61M 5/1408* (2013.01); *F16K 15/144* (2013.01);
(Continued)

(58) Field of Classification Search
CPC ........... A61M 5/1408; A61M 2039/242; Y10T 137/789; Y10T 137/7838; Y10T 137/87684; F16K 15/148
See application file for complete search history.

(56) References Cited

U.S. PATENT DOCUMENTS 155,668 A * 10/1874 Painter .................. F16K 15/148
137/512.1
155,669 A * 10/1874 Painter .................. F16K 15/148
137/854
(Continued)

FOREIGN PATENT DOCUMENTS

EP 1570872 A1 9/2005
EP 2446177 B1 9/2013
(Continued)

OTHER PUBLICATIONS

Office Action received for European Patent Application No. 13769183.8, dated Feb. 4, 2016, 5 pages.
(Continued)

*Primary Examiner* — Atif Chaudry
(74) *Attorney, Agent, or Firm* — Wood IP LLC

(57) ABSTRACT

The present invention relates to a device (1) for delivery of fluid, said device comprising at least two fluid ducts (12-17) of flexible material, each of which in one end can be connected to a fluid source and in the opposite end is connected to a manifold (18) having an inlet end and an outlet end, each of said fluid ducts (12-17) comprising a pinch valve (19) for closing and opening the duct. According to the invention a check valve (20) is disposed in at least one of said fluid ducts (12-17) in the end thereof connected to the manifold (18).

20 Claims, 5 Drawing Sheets

(51) Int. Cl.
*A61M 5/14* (2006.01)
*F16K 27/02* (2006.01)
*A61M 39/24* (2006.01)
*B01D 15/14* (2006.01)

(52) U.S. Cl.
CPC .......... *F16K 15/145* (2013.01); *F16K 15/148* (2013.01); *F16K 27/0209* (2013.01); *A61M 2039/242* (2013.01); *B01D 15/14* (2013.01); *Y10T 137/789* (2015.04); *Y10T 137/7838* (2015.04); *Y10T 137/87684* (2015.04)

(56) References Cited

U.S. PATENT DOCUMENTS

| | | | |
|---|---|---|---|
| 1,306,391 | A * | 6/1919 | Romanoff ............. F16K 15/148 137/512.15 |
| 2,254,994 | A | 9/1941 | Butland |
| 2,913,000 | A | 11/1959 | Roberts |
| 2,954,028 | A | 9/1960 | Smith |
| 2,999,499 | A | 9/1961 | Willet |
| 3,572,375 | A | 3/1971 | Rosenberg |
| 4,666,429 | A | 5/1987 | Stone |
| 4,915,688 | A | 4/1990 | Bischof et al. |
| 5,098,405 | A | 3/1992 | Peterson et al. |
| 5,207,642 | A | 5/1993 | Orkin et al. |
| 5,356,375 | A | 10/1994 | Higley |
| 5,431,202 | A | 7/1995 | Dikeman et al. |
| 5,738,662 | A | 4/1998 | Shannon et al. |
| 6,508,791 | B1 | 1/2003 | Guerrero |
| 7,901,386 | B2 | 3/2011 | Hishikawa et al. |
| 8,726,938 | B2 | 5/2014 | Kern |
| 2003/0042187 | A1 * | 3/2003 | Menne ................ A61M 1/0001 210/136 |
| 2006/0211981 | A1 * | 9/2006 | Sparks .................. A61M 1/101 604/44 |
| 2007/0083677 | A1 | 4/2007 | Cecka et al. |
| 2007/0282297 | A1 | 12/2007 | Knight |
| 2009/0116938 | A1 | 5/2009 | Wakabayashi |

FOREIGN PATENT DOCUMENTS

| | | |
|---|---|---|
| EP | 1893273 B1 | 6/2014 |
| GB | 2 274 148 | 7/1994 |
| JP | 2004-173844 A | 6/2004 |
| JP | 2004-197766 A | 7/2004 |
| JP | 2005-114062 A | 4/2005 |
| JP | 2008-540056 A | 11/2008 |
| JP | 2009-115205 A | 5/2009 |
| JP | 5688644 B2 | 3/2015 |
| WO | 2004/047887 A1 | 6/2004 |
| WO | 2007/030162 A2 | 3/2007 |
| WO | WO 2010/149145 | 12/2010 |
| WO | 2013/147697 A1 | 10/2013 |

OTHER PUBLICATIONS

Office Action received for Japanese Patent Application No. 2015-503163 dated Feb. 7, 2017, 4 pages. (English translation only).
International Preliminary Report on Patentability received for PCT Patent Application No. PCT/SE2013/050357, dated Oct. 1, 2014, 10 pages.
International Search Report and Written Opinion received for PCT Patent Appliation No. PCT/SE2013/050357, dated Jul. 26, 2013, 16 pages.

* cited by examiner

DEVICE FOR DELIVERY OF SAMPLE FLUID

CROSS-REFERENCE TO RELATED APPLICATIONS

This application is a filing under 35 U.S.C. 371 of international application number PCT/SE2013/050357, filed Mar. 28, 2013, published on Oct. 3, 2013 as WO 2013/147697, which claims priority to application number 1250318-1 filed in Sweden on Mar. 30, 2012.

TECHNICAL FIELD

The present invention relates to a device for delivery of fluid, said device comprising at least two fluid ducts of flexible material, each of which in one end can be connected to a fluid source and in the opposite end is connected to a manifold having an inlet end and an outlet end, each of said fluid ducts comprising a pinch valve for closing and opening the duct. The invention also relates to an insertable check valve useful in the device.

BACKGROUND OF THE INVENTION

Pinch valve operated delivery devices of the above mentioned type are for example used in single-use liquid handling systems applied in the biotechnology or medical field. Single-use systems employ typically pre-sterilized components that are in fluid contact with the processing fluid. Such components are preferably made from incinerable plastics materials and are often disposed of after use to avoid cleaning prior to re-use and related cleaning validation. By having the disposable components pre-sterilized and cleanroom manufactured, all cleaning and cleaning validation prior to processing is also eliminated. Sterilization methods are usually gamma irradiation, E-beam sterilization, autoclaving but other methods exist. Pinch valves are often used with such disposable single-use components due to the simple and cost-effective principle. In manufacturing of biopharmaceuticals for example, such single-use systems are adapted for liquid handling in filtration and chromatography, chromatography systems, such as the ÄKTA™ ready system from GE Healthcare, Sweden, for example.

Due to the design principle of pinch valves such devices suffer from dead volumes caused by minimum length of tubing required when pinch valves are arranged in fluid manifolds. This problem arises especially at systems used in production scale employing higher flow rates as this requires fluid lines of larger diameter and increased dimensions of tubing and components. Typically, tubing in production scale equipment has an inner diameter of ¼ "(6.25 mm) or larger. With such larger diameter tubing, an increasing risk for convective mixing of fluid in manifolds exists. In FIG. 1, such a device is schematically shown having six fluid ducts A connected to a manifold B. A pump P sucks fluid from the manifold B. A pinch valve C is disposed in each of the fluid ducts A. In FIG. 1, if the outer pinch valve on the left side is opened, fluid from this opened fluid duct flows through the manifold B through the pump P and is delivered to the system. However, on its way to the pump P, the fluid from the opened fluid duct will also reach into the space d in the other fluid ducts between the manifold B and the respective closed pinch valve C. Due to these dead volumes the device cannot be rinsed effectively and there is a risk for contamination and carry over when running fractions and sequential protocols such as in chromatography. The objective of the present invention is to eliminate or at least greatly reduce said risk.

SUMMARY OF THE INVENTION

This objective is accomplished by a device for delivery of fluid, said device comprising at least two fluid ducts of flexible material, each of which in one end can be connected to a fluid source and in the opposite end is connected to a manifold having an inlet end and an outlet end, each of said fluid ducts comprising a pinch valve for closing and opening the duct, characterized in that a check valve is disposed in at least one of said fluid ducts in the end thereof connected to the manifold. Said check valves allow only fluid transport in one direction and thereby can fluid from the manifold not enter the spaces between the manifold and a closed pinch valve in the respective fluid duct.

In a preferred embodiment, the check valve of the fluid duct situated nearest the inlet end of the manifold as seen in a direction from the inlet end to the outlet end of the manifold is disposed up-stream of and close to the adjacent fluid duct.

In a further preferred embodiment, a further check valve is disposed in the manifold up-stream of and close to each of said fluid ducts being situated nearer the outlet end of the manifold than the two fluid ducts nearest the inlet end of the manifold. By such a measure fluid delivered from an open fluid duct into the manifold is prevented from moving in a direction from the outlet end of the manifold towards the inlet end thereof.

Each fluid duct is preferably connected to the manifold by T-connectors and the check valve of each fluid duct is disposed inside the T-connector.

The device for delivery of fluid is preferably of a single-use disposable type which preferably is pre-sterilized.

In a preferred embodiment, the check valves are flap valves.

In a further preferred embodiment, the check valves are single-use disposable valves.

In a further preferred embodiment, the closing force of the check valves is lower in the open state thereof than in the closed state.

BRIEF DESCRIPTION OF THE DRAWINGS

The invention will now be described with reference to the enclosed drawings, in which.

DESCRIPTION OF EMBODIMENTS

Figure 3:
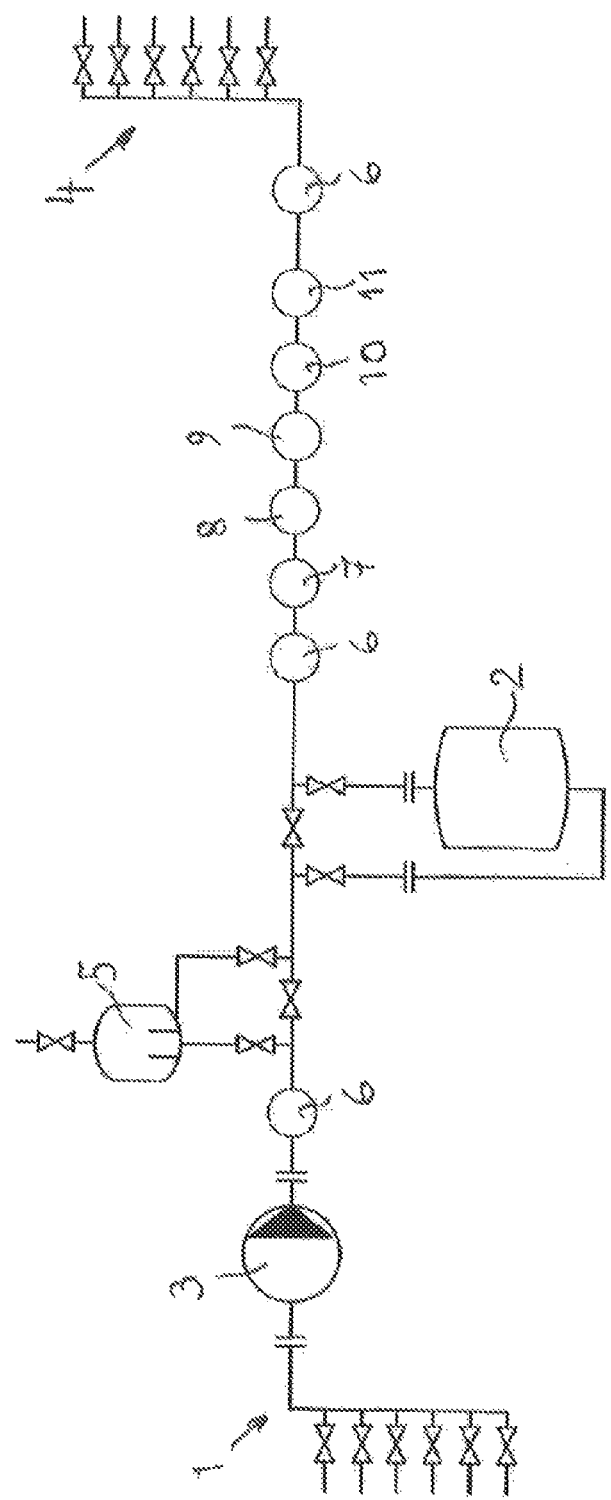

In FIG. 3, the configuration of a chromatography system is schematically shown. This system comprises a device 1 for delivery of fluid from one of several fluid ducts in the device to a column 2 with the aid of a pump 3. An automated pinch valve is disposed in each of the fluid ducts of the device 1. From column 2, the fluid is transported to a device 4 for delivery of the received fluid to one of several fluid ducts in this device. The system also comprises an air trap 5 through which the fluid can pass before it is transported to the column 2, several pressure sensors 6, a pH cell 7, a flow meter 8, a temperature measuring device 9, a conductivity cell 10 and an UV cell 11. Furthermore, the system comprises valves enabling by-pass of the air trap 5 and/or the column 2. The system also comprises control system for controlling the opening and closing of the valves according to a selected protocol for sequential delivery of different fluids to the column. The system per se is not part of the present invention but only used as example of a system in which a device 1 for delivery of fluid according to the present invention can be incorporated.

Figure 1:
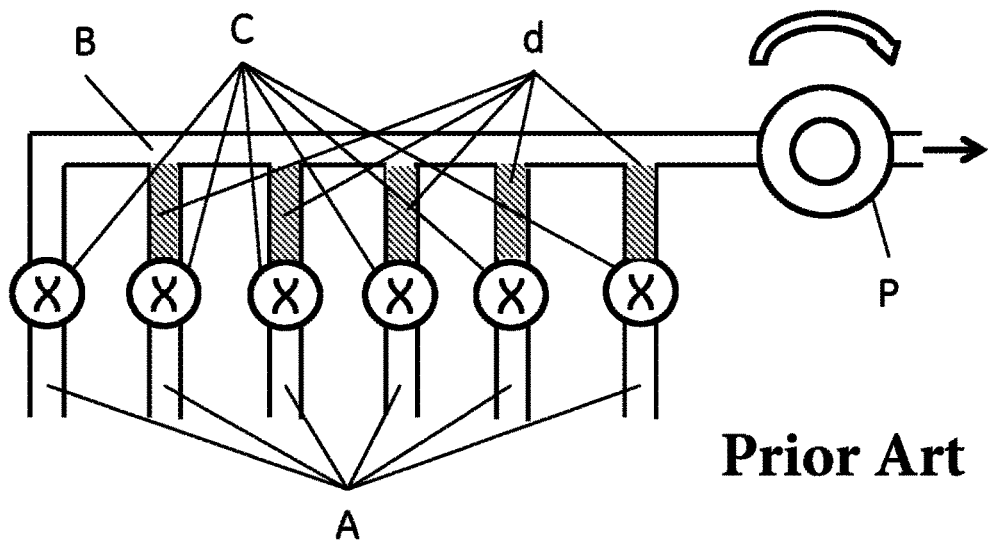
FIG. 1 schematically shows a device for delivery of fluid according to prior art, FIG. 2 schematically shows a device for delivery of fluid according to a preferred embodiment of the invention, and FIG. 3 schematically shows a chromatography system in which a device according to FIG. 2 can be incorporated.
Figure 2:
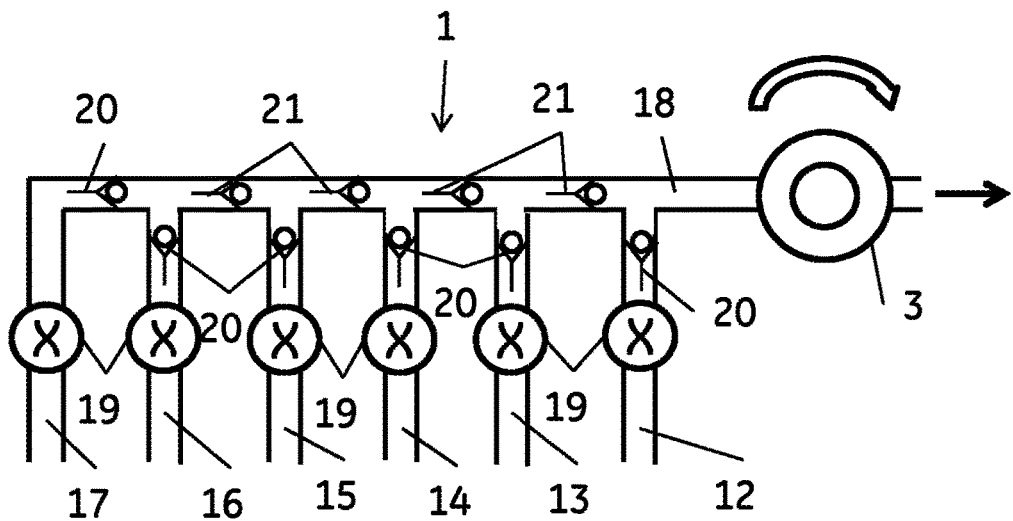

In FIG. 2, such a device 1 for delivery of a selected fluid to the column 2 with the aid of the system pump 3 is schematically shown. The device 1 comprises six fluid ducts 12-17 each of which in one end is connected to a fluid source (not shown). In the opposite end, each of the fluid ducts 12-17 is connected to a manifold 18 which in turn in the outlet end thereof is connected to the pump 3. The fluid ducts 12-17 are made of flexible material and a pinch valve 19 is disposed in each fluid duct 12-17 near its connection to the manifold 18. The pinch valves 19 operate between a closed state in which the opposite sides of the wall of the flexible duct are pressed together and a fully open state. In order to enable such pressing together of the opposite sides of the wall of a fluid duct, the pinch valves must be distanced from the connection to the manifold 18. Furthermore, if the ducts are connected to the manifold 18 via T-shaped barb connectors, the pinch valves must also be distanced from the ends of such T-shaped barb connectors. In each case, the ends of the fluid ducts 12-17 will comprise an end space open to the manifold 18 independent of if the respective pinch valve 19 is closed or opened, similar to space d in FIG. 1. As mentioned earlier such open spaces creates a risk for contamination of the fluid from the different fluid ducts as well as carry over, for example due to diffusion and/or pulsation-induced convection phenomena, when running fractions and sequential protocols such as in chromatography. This is particularly the case when high flow rates typical of bio-processing operations (typically 1-10 L/min) are applied using pulsating pumps such as high-flow peristaltic pumps. Under such conditions significant in-mixing from stagnant fluid in the ducts can occur within one minute. For bioprocess use, the pump 3 typically is a peristaltic pump capable of delivering a flow rate of at least 100 mL/min, such as at least 1 L/min or 1-10 L/min Such pumps are available e.g. under the trade name Masterflex™ from Cole-Parmer Instrument Company Ltd (UK). The fluid ducts 12-17, as well as the manifold 18 and any tubing connected to the device can in this case suitably have inner diameters of at least 6 mm.

According to the present invention check valves 20 are disposed in the ends of the fluid ducts 12-17 at the connections to the manifold 18. By "check valves" is meant valves that only allow transport of fluid in one direction, i.e. in a direction towards the pump 3 in the embodiment shown in FIG. 2. The check valves 20 ensure that fluid in the manifold 18 cannot flow into the spaces in the fluid ducts 12-17 between the respective pinch valve 20 and the manifold 18 when the respective pinch valve 12-17 is closed. However, when a pinch valve 20 in a fluid duct 12-17 is opened, fluid from the opened fluid duct 12-17 is allowed to flow into the manifold 18 in the direction towards the pump 3. Thereby, the risk for contamination and carry over of the fluid flowing in the manifold and eventually fed to the column 2 is eliminated or at least greatly reduced. Optionally, check valves 21 are also disposed in the manifold 18 immediately up-stream of fluid ducts 12-15. The check valves prevent fluid from an open fluid duct 12-17 from moving in a direction towards the inlet end (the left end in FIG. 2) of the manifold 18. Such movement might otherwise occur for example due to diffusion and/or pulsation-induced convection phenomena. When for example the feeding of fluid from fluid duct 12 to the column 2 is interrupted by closing of the pinch valve 19 in this fluid duct and the pinch valve 19 in fluid duct 13 is opened for feeding fluid to column 2, the fluid from fluid duct 12 that is remaining in the manifold 18 will reach the pump 3 first followed by the fluid from the now opened fluid duct 13. Since no fluid from fluid duct 12 has been able to reach into the manifold 18 in the space between fluid ducts 12 and 13, a clear border is created between the successive flows of fluids from fluid ducts 12 and 13 that reach the pump 3 There will only be an insignificant mixing, if any, of the fluids in the border zone between the fluids from fluid ducts 12 and 13. It is to be observed that the check valve 20 in the fluid duct 17 is disposed in the inlet end of the manifold immediately up-stream of fluid duct 16 and thereby fulfils the same function as check valves 21 as well as preventing fluid from gathering in the space of the fluid duct 17 between the pinch valve 19 and the manifold 18.

In the described embodiment six fluid ducts are comprised in the device 1 but it is of course possible to use more or fewer fluid ducts connected to the manifold 18.

Equipment used for separation and purification of biomedical products must fulfil strict cleanliness demands. The cleaning validation of re-used equipment, such as chromatography systems, may easily be more costly than the equipment itself. To reduce the need for cleaning validation, the pharmaceutical and biotech industries are increasingly using pre-sterilized, single-use plastic tubing and collapsible plastic bags for liquid transfer and storage. The device for delivery of fluids in the ÄKTA™ ready system from GE Healthcare, Sweden, is of the single-use type as well as the described device for delivery of fluid according to the present invention.

The described embodiment of the device for delivery of fluid can have T-shaped connectors or Y-shaped connectors for coupling the fluid ducts to the manifold.

However, other types of devices for fluid delivery can be used, for example devices made by a molding procedure. Such molded devices are commercially available from New-Age® Industries, Inc, USA, and need no T-shaped or Y-shaped connectors. In the described embodiment, the fluid ducts are disposed in a row. It is also possible to have two or more rows of fluid ducts disposed in different planes connected to the manifold, whereby the manifold in such a case have two or more connections for the different fluid ducts around its circumference at the junction place for these fluid ducts. The manifold could also be made from a machined or molded block having openings for the connection of the ends of the flexible fluid ducts. The manifold can also be made from an assembly of several smaller such blocks.

The invention is thus not restricted to the described embodiment but encompass all fluid delivery devices of the type in which pinch valves are used for closing and opening of a fluid duct of flexible material.

The device 4 for delivery of fluid differs from the device 1 for delivery of fluid mainly in that the fluid in the manifold flows from the manifold into one of the fluid ducts, i.e. a fluid duct having its pinch valve in an open state. Also in this case check valves similar to check valves 20 in the device 1 are needed.

In all embodiments described above parts and surfaces being in contact with a process fluid are suitably selected from materials that are in accordance with typical material requirements in (bio-)pharmaceutical manufacturing or food grade quality. For example, materials are suitably in compliance with USP Class VI and 21 CFR 177. Furthermore they are suitably of animal-free origin and compliance to EMEA/41O/01.

The components in devices 1 and 4 can be similar to similar components in the ÄKTA™ ready system from GE Healthcare, Sweden. Thus, the fluid ducts and the manifold can be made from silicone tubing and the possible T-shaped barb connectors can be made from polypropylene or polyvinylidene fluoride. Other plastic materials having similar properties can of course be used.

The pinch valves can be single-use disposable valves of the type used in the ÄKTA™ ready system but other types of pinch valves can be used, such as pinch valves from Acro Associates, Inc., US.

Also the check valves can preferably be single-use disposable valves opening when a certain pressure is applied, for example of the type known from face masks, alcohol tester mouthpieces or the like. Other types of check valves that can be used are "Rubber Duckbill" check valves.

The check valves can also be designed such that the closing force of the valve is reduced once the valve has opened, hereby reducing the throttling and pressure loss over the check valve when operating the valve in open position. Such designs can for example employ magnets that keep the valve in closed position but in the open position the magnet force is reduced due to the increased distance and reduced magnetic closing force between corresponding parts. Other mechanical design solutions could be employed to achieve the same effect of such a "smart valve".

Also butterfly valves or flap valves can be used, the opening and closing thereof synchronized with the opening and closing of the pinch valve in the same fluid duct.

Also, valves can be designed such that two-check valve functions are inter-related by mechanical or magnetic principles such that the flow in one duct is causing the closing of another adjacent duct and the corresponding check valves function.

The embodiment of the inventive fluid delivery device 1 according to FIG. 2 has been described in connection with incorporating into a chromatography system but the fluid delivery device 1 can of course be incorporated in any system in which delivery of different fluids in sequential order occurs.

Figure 4:
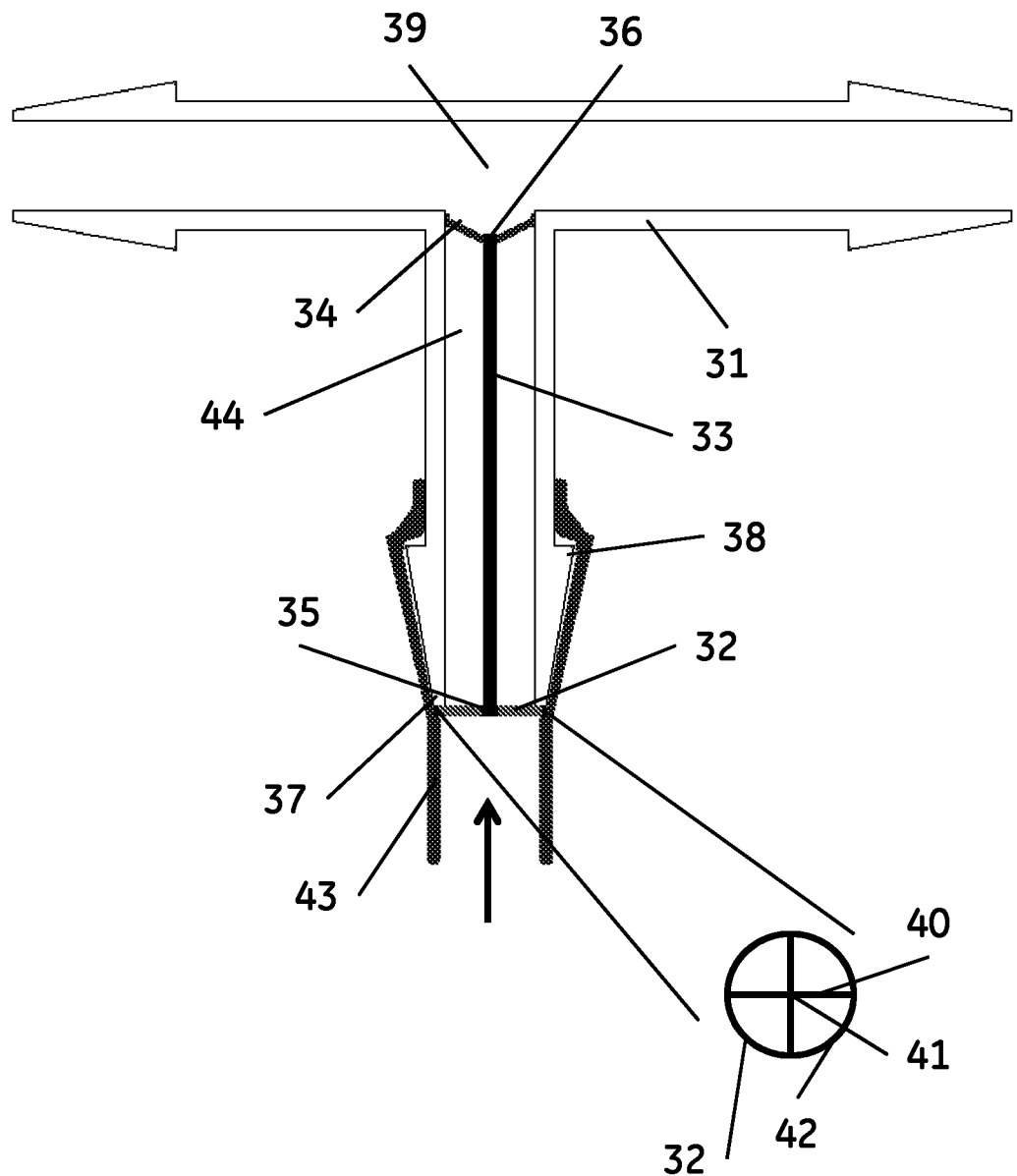
FIG. 4. schematically hows an insertable check valve according to the invention, inserted in a T-connector with hose barbs.
Figure 5:
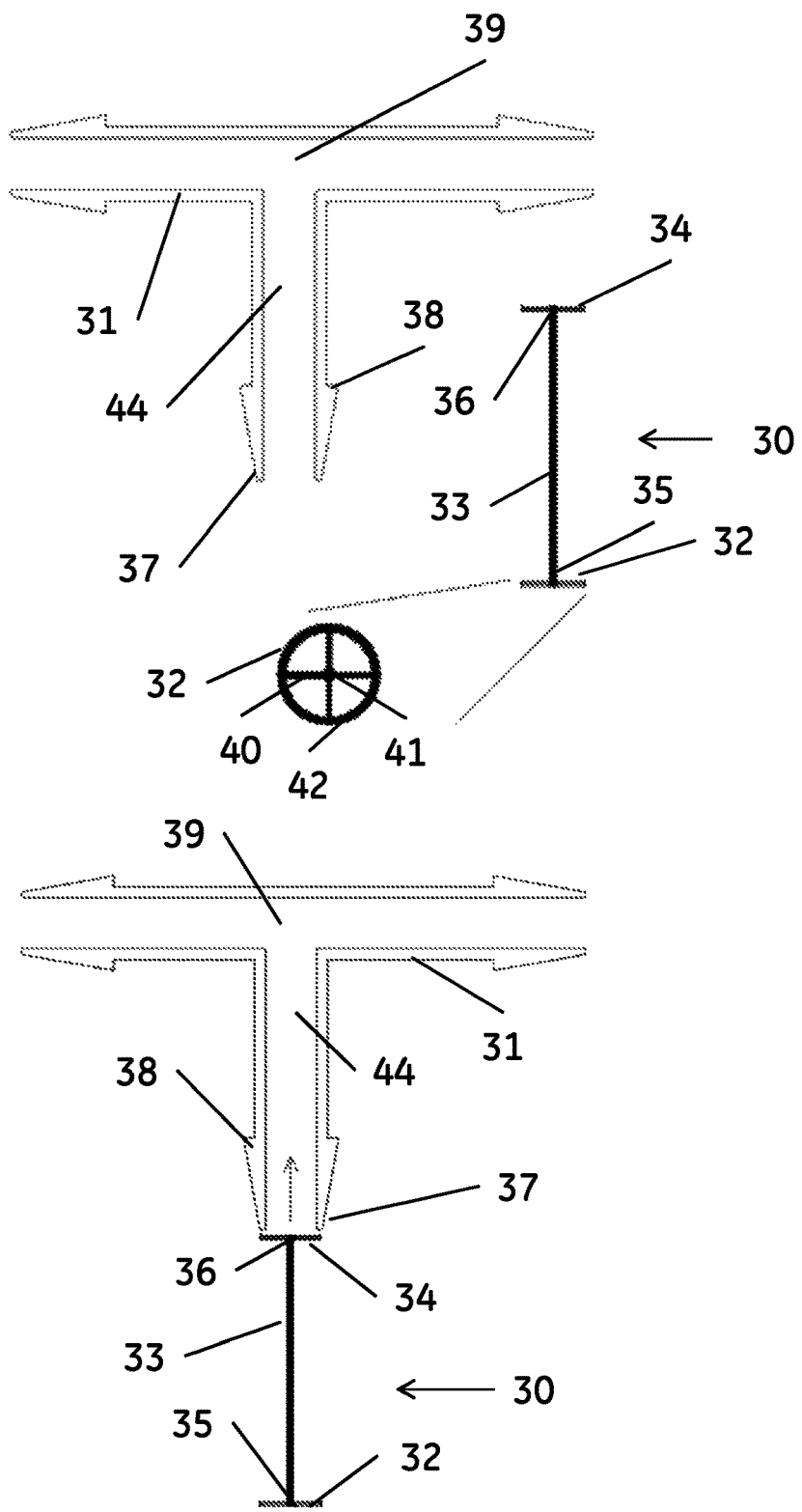
FIG. 5 schematically shows the first steps of insertion of the check valve according to FIG. 4 in a T-connector.
Figure 6:
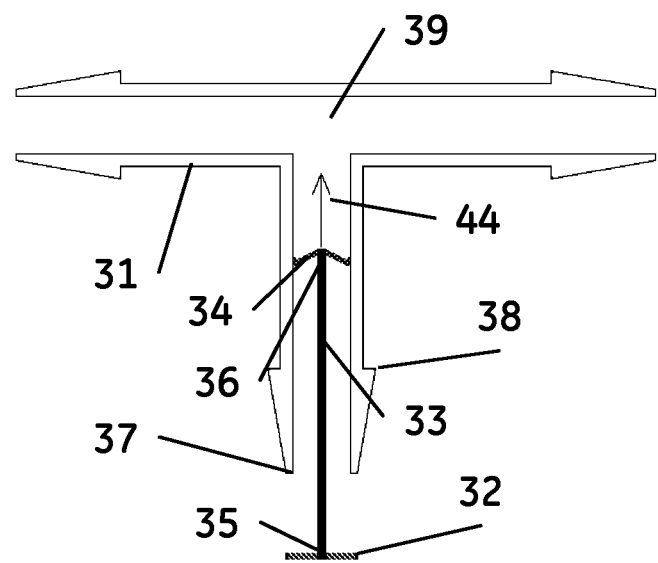
FIG. 6 schematically shows the last steps of of insertion of the check valve according to FIG. 4 in a T-connector.
Figure 6:
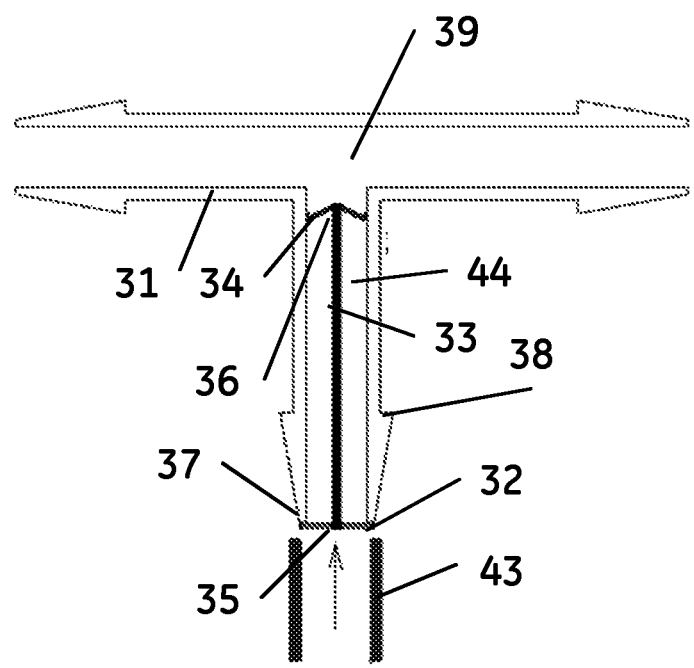

In one embodiment of the device, illustrated by FIGS. 4-6, at least one check valve 20;30, such as all the check valves, is inserted in a fluid duct/connector leg 44 and comprises an anchoring element 32, a connector rod 33 and an elastomeric flap disc 34, wherein the anchoring element is arranged at one end 35 of the connector rod and the flap disc is arranged orthogonally to the connector rod in proximity of an opposite end 36 of the connector rod. In this embodiment, fluid duct/connector leg 44 can represent any one of the fluid ducts 12-17 (in particular the portions of these ducts between respective pinch valve 20 and manifold 18) and/or a portion of the manifold 18. The anchoring element 32 holds the check valve in place, e.g. by being engaged with a port end 37 of the fluid duct/connector leg 44 and a length of tubing 43 attached to the port end 37. The anchoring element is preferably hollow to allow unimpeded fluid flow past it. The elastomeric flap disc is preferably circular with a diameter equal to or slightly lower than the internal diameter of the fluid duct/connector leg 44, such as 90-99 or 95-99% of the internal diameter. The elastomeric flap disc is constructed with a thickness and hardness such that in the absence of a flow through fluid duct/connector leg 44 it has an essentially planar shape and closes fluid duct/connector leg 44 from the other legs of the T-connector. When fluid is supplied through fluid duct/connector leg 44, the disc will however deflect and let the flow pass. The anchoring element keeps the chek valve in place and has a diameter slightly larger than the inner diameter of fluid duct/connector leg 44. It can e.g. have a diameter equal to or approximately equal to the outer diameter of port end 37.

The fluid duct/connector leg 44 may be a part of a hose-barb connector 31, where the check valve is inserted with the anchoring element at a port end 37 of the hose barb 38 and the elastomeric flap disc in proximity of a junction point 39 of the connector. This minimizes the dead volume in fluid duct/connector leg 44, as the flap disc closes the leg at the junction or close to the junction.

In some embodiments the anchoring element 32 is circular with a plurality of spokes 40 extending from a hub 41 to a circular rim 42. This construction allows a firm anchoring, without impeding the flow through fluid duct/connector leg 44. The connector rod 33 preferably extends from the hub 41.

The elastomeric flap disc 34 can e.g. be manufactured from silicone rubber of Shore A hardness 10-90, such as 25-60. The hardness is measured by a durometer according to methods well known in the art. The disc may be planar or tapered and may further comprise one or more recesses acting as hinges for the disc to facilitate deflection in the flow direction (i.e. towards the junction).

In some embodiments the inserted check valve 20;30 further comprises a support element between the elastomeric flap disc and the anchoring element, adjacent to the elastomeric flap disc. Such a support element will be hollow to allow flow through leg 44 and can e.g. be circular with a plurality of spokes extending from a hub to a circular rim, i.e. similar to the anchoring element 32, but with a diameter smaller than the inner diameter of fluid duct/connector leg 44 to allow insertion into the leg. The support element prevents deflection of the flap disc in the direction from the junction and enables a unidirectional check valve function also if higher pressures are applied to the junction side of the flap disc.

In a further aspect of the invention, as illustrated by FIGS. 4-6, a check valve insertable in a connector is disclosed, which comprises an anchoring element 32, a connector rod 33 and an elastomeric flap disc 34, wherein the anchoring element is arranged at one end 35 of the connector rod and the flap disc is arranged orthogonally to the connector rod in proximity of the opposite end 36 of the connector rod. The connector into which the check valve is insertable is typically a connector for flexible tubing, it may have hose barbs or other attachment means for flexible tubing and it may be e.g. a T-connector, a Y connector, a two-way linear connector or a multi-port connector. Further details about the check valve construction are given in the above embodiments. This insertable check valve can be used in the devices of the invention but it is also generally useful whenever the direction of flow needs to be controlled in a connector.

In some embodiments the anchoring element can be circular with a plurality of spokes 40 extending from a hub 41 to a circular rim 42.

In some embodiments the elastomeric flap disc is manufactured from silicone rubber of Shore A hardness 10-90, such as 25-60.

In some embodiments the check valve further comprises a support element (not shown) between the elastomeric flap disc 34 and the anchoring element 32, adjacent to the elastomeric flap disc 34.

The invention claimed is:

1. A device for delivery of fluid, said device comprising
at least two fluid ducts of flexible material having substantially the same inner diameter throughout the entire length of the duct, each of which in one end can be connected to a fluid source and in the opposite end connected to a manifold having an inlet end and an outlet end, and
at least one of said fluid ducts is connected to the manifold by a T-shaped hose-barb connector and comprises a pinch valve for closing and opening the duct and a check valve disposed in the at least one of said fluid ducts in the end thereof connected to the manifold between the pinch valve and the manifold,
wherein the check valve comprises an anchoring element, an elastomeric flap disc, and a connector rod connecting the anchor element and the flap disc,
wherein the anchoring element is connected at one end of the connector rod and the flap disc is connected to the opposite end of the connector rod, such that in resting state, the side cross sectional view of the check valve is in the shape of an "I" with the check valve inserted with the anchoring element at a port end of the T-shaped hose-barb and the elastomeric flap disc in proximity of the junction point of the T-shaped hose-barb connector such that the flap disc sealing directly against the wall of the duct.

2. The device of claim 1, wherein the check valve of the fluid duct situated nearest the inlet end of the manifold as seen in a direction from the inlet end to the outlet end of the manifold is disposed in the manifold up-stream of and close to the adjacent fluid duct.

3. The device of claim 2, further comprising a check valve disposed in the manifold up-stream of and close to each of said fluid ducts being situated nearer the outlet end of the manifold than the two fluid ducts nearest the inlet end of the manifold.

4. The device of claim 1, wherein the device is of a single-use disposable type.

5. The device of claim 1, wherein the device is pre-sterilized.

6. The device of claim 1, wherein the closing force of the check valves is lower in the open state thereof than in the closed state.

7. The device of claim 1, wherein the anchoring element is circular with a plurality of spokes extending from a hub to a circular rim.

8. The device of claim 1, wherein the elastomeric flap disc is manufactured from silicone rubber of Shore A hardness between 10 and 90.

9. The device of claim 8, wherein the elastomeric flap disc is manufactured from silicone rubber of Shore A hardness between 25 and 60.

10. The device of claim 1, wherein the at least one check valve further comprises a support element between the elastomeric flap disc and the anchoring element, adjacent to the elastomeric flap disc.

11. The device of claim 1, wherein the device is pre-sterilized and of a single-use disposable type.

12. A check valve insertable in a hose-barb connector, wherein the hose-barb connector comprises a junction point formed by a horizontal duct intersecting with a vertical duct having an inner diameter that is substantially the same throughout the entire length of the vertical duct and a port end at the end of the vertical duct, the check valve comprising
an anchoring element,
an elastomeric flap disc, and
a connector rod connecting the anchor element and the flap disc,
wherein the anchoring element is connected at one end of the connector rod and the flap disc is connected to the opposite end of the connector rod, such that in resting state, the side cross sectional view of the check valve is in the shape of an "I", and
wherein the check valve can be inserted with the anchoring element at the port end of the hose-barb and the elastomeric flap disc in proximity of the junction point of the hose-barb connector such that flap disc seals directly against the wall of the vertical duct.

13. The check valve of claim 12, wherein the anchoring element is circular with a plurality of spokes extending from a hub to a circular rim.

14. The check valve of claim 12, wherein the elastomeric flap disc is manufactured from silicone rubber of Shore A hardness between 10 and 90.

15. The check valve of claim 12, further comprising a support element between the elastomeric flap disc and the anchoring element, adjacent to the elastomeric flap disc.

16. The check valve of claim 12, wherein the elastomeric flap disc is manufactured from silicone rubber of Shore A hardness between 25 and 60.

17. The check valve of claim 12, wherein the check valve is pre-sterilized and of a single-use disposable type.

18. A device for delivery of fluid, said device comprising
at least two fluid ducts of flexible material having substantially the same inner diameter throughout the entire length of the duct, each of which in one end can be connected to a fluid source and in the opposite end connected to a manifold having an inlet end and an outlet end,
at least one of said fluid ducts is connected to the manifold by a T-shaped hose-barb connector and comprises a pinch valve for closing and opening the duct and a check valve disposed in the each one of said fluid ducts in the end thereof connected to the manifold between the pinch valve and the manifold, wherein the check valve of the fluid duct situated nearest the inlet end of the manifold as seen in a direction from the inlet end to the outlet end of the manifold is disposed in the manifold up-stream of and close to the adjacent fluid duct, and
an additional check valve disposed in the manifold up-stream of and close to each of said fluid ducts being situated nearer the outlet end of the manifold than the two fluid ducts nearest the inlet end of the manifold,
wherein the check valve comprises an anchoring element, an elastomeric flap disc, and a connector rod connecting the anchor element and the flap disc, wherein the anchoring element is connected at one end of the connector rod and the flap disc is connected to the opposite end of the connector rod, such that in resting state, the side cross sectional view of the check valve is in the shape of an "I" with the check valve inserted with the anchoring element at a port end of the T-shaped hose-barb and the elastomeric flap disc in proximity of a junction point of the hose-barb connector such that the flap disc sealing directly against the wall of the duct.

19. The device of claim 18, wherein the device is of a pre-sterilized, single-use disposable type with the elastomeric flap disc manufactured from silicone rubber of Shore A hardness between 25 and 60.

20. The device of claim 18, wherein the device is pre-sterilized and of a single-use disposable type.

* * * * *